United States Patent [19]

Finkel et al.

[11] Patent Number: 4,702,378
[45] Date of Patent: Oct. 27, 1987

[54] SANITARY, DISPOSABLE BABY CHANGE KIT

[76] Inventors: Henry Finkel, 342 Elm Avenue, Westmount, Quebec, Canada, H3Z 1Z5; Allan Thomas, 5518 Silverson Avenue, Montreal, Quebec, Canada, H4V 2G5

[21] Appl. No.: 913,245

[22] Filed: Sep. 30, 1986

[51] Int. Cl.4 ............................................ B65D 30/22
[52] U.S. Cl. ...................................... 206/581; 206/38; 383/38; 383/40
[58] Field of Search ............................. 383/38, 39, 40; 206/581, 38, 235

[56] References Cited

U.S. PATENT DOCUMENTS

| 578,243 | 3/1897 | Keith | 383/38 |
|---|---|---|---|
| 1,606,115 | 11/1926 | Williams . | |
| 1,688,699 | 10/1928 | Gardner, Jr. | 383/38 |
| 1,723,740 | 8/1929 | Lewis . | |
| 2,447,940 | 8/1948 | Holland . | |
| 2,533,850 | 12/1950 | Syracuse . | |
| 2,537,196 | 1/1951 | Tanski | 383/40 |
| 2,869,604 | 1/1959 | Fitzsimmons | 383/40 |
| 3,389,784 | 6/1968 | Hendricks et al. . | |
| 3,762,628 | 10/1973 | Sargent | 383/40 |
| 3,780,857 | 12/1973 | Rosano, Jr. et al. . | |
| 3,827,552 | 8/1974 | Janhonen | 383/38 |
| 3,967,666 | 7/1976 | Farrar | 383/39 |
| 4,154,323 | 5/1979 | Sneider | 383/40 |
| 4,221,221 | 9/1980 | Ehrlich . | |
| 4,228,900 | 10/1980 | Lambach et al. . | |
| 4,391,370 | 7/1983 | Dalbo | 383/40 |
| 4,574,822 | 3/1986 | Helinsky . | |

Primary Examiner—Joseph Man-Fu Moy
Attorney, Agent, or Firm—Martin P. Hoffman; Mitchell B. Wasson; Charles W. Fallow

[57] ABSTRACT

A single use, disposable kit receives, and retains, toiletries and a diaper for the care of a baby in a sanitary, tamper-proof fashion. The kit is executed in a thin plastic film that is folded over upon itself so that the toiletries and diaper are enveloped within the interior of the kit and are protected against degradation.

3 Claims, 5 Drawing Figures

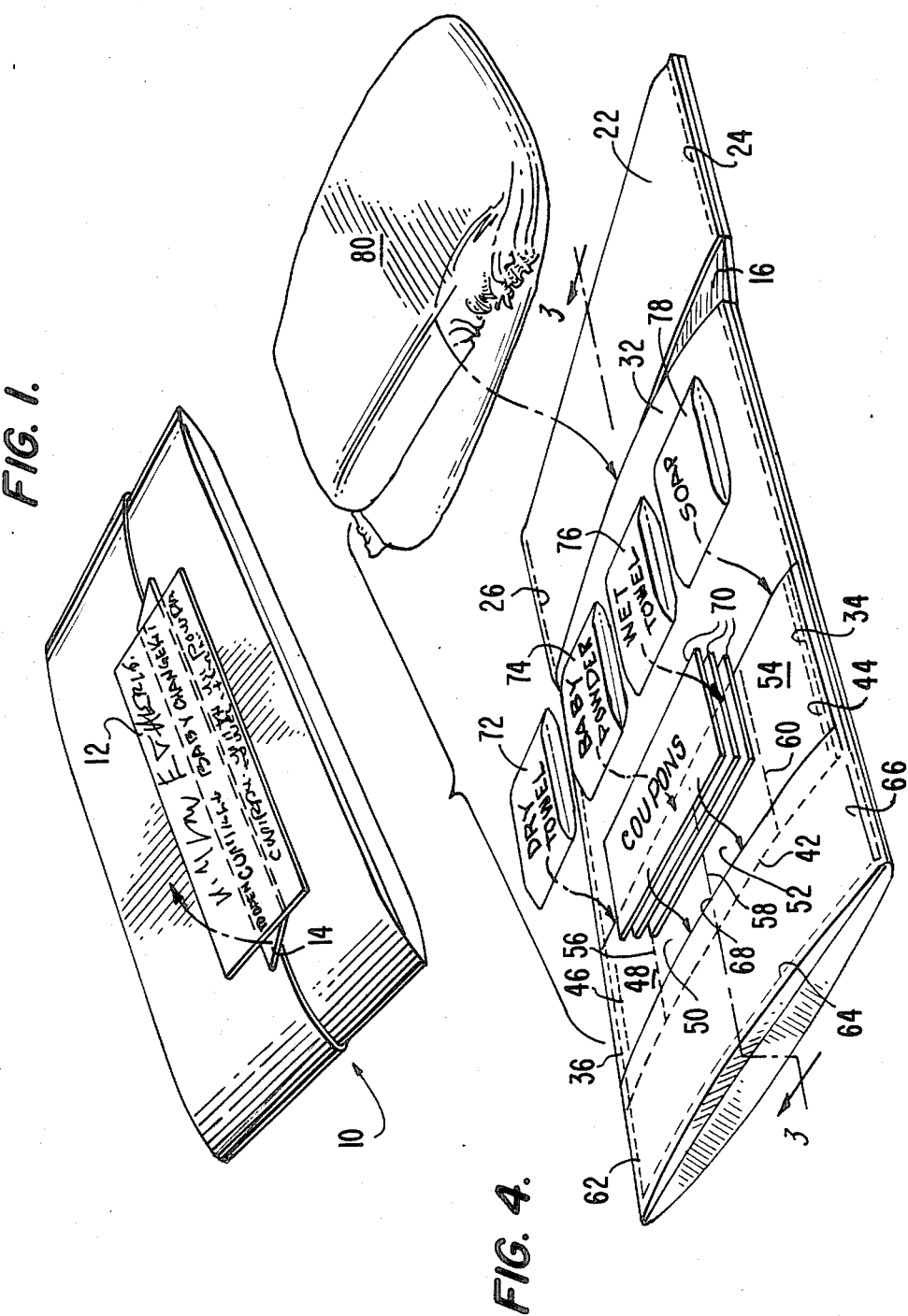

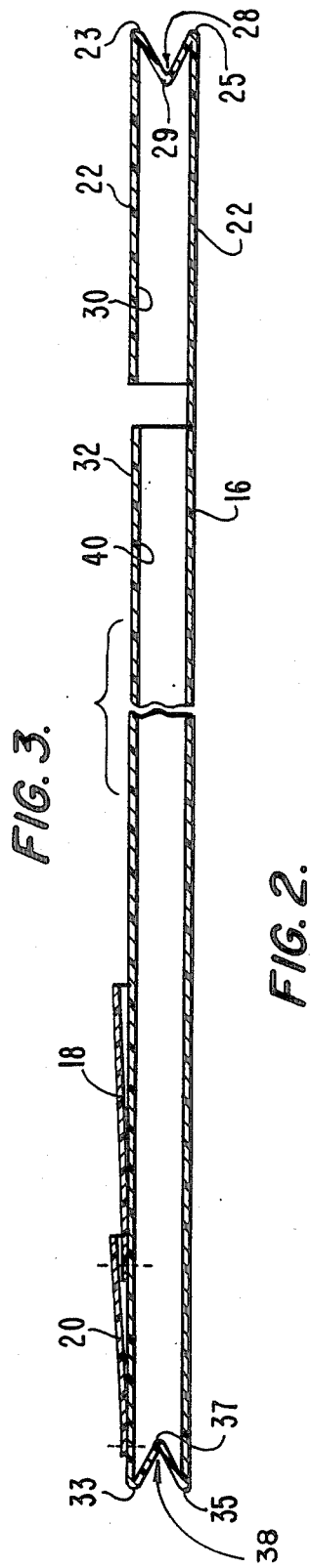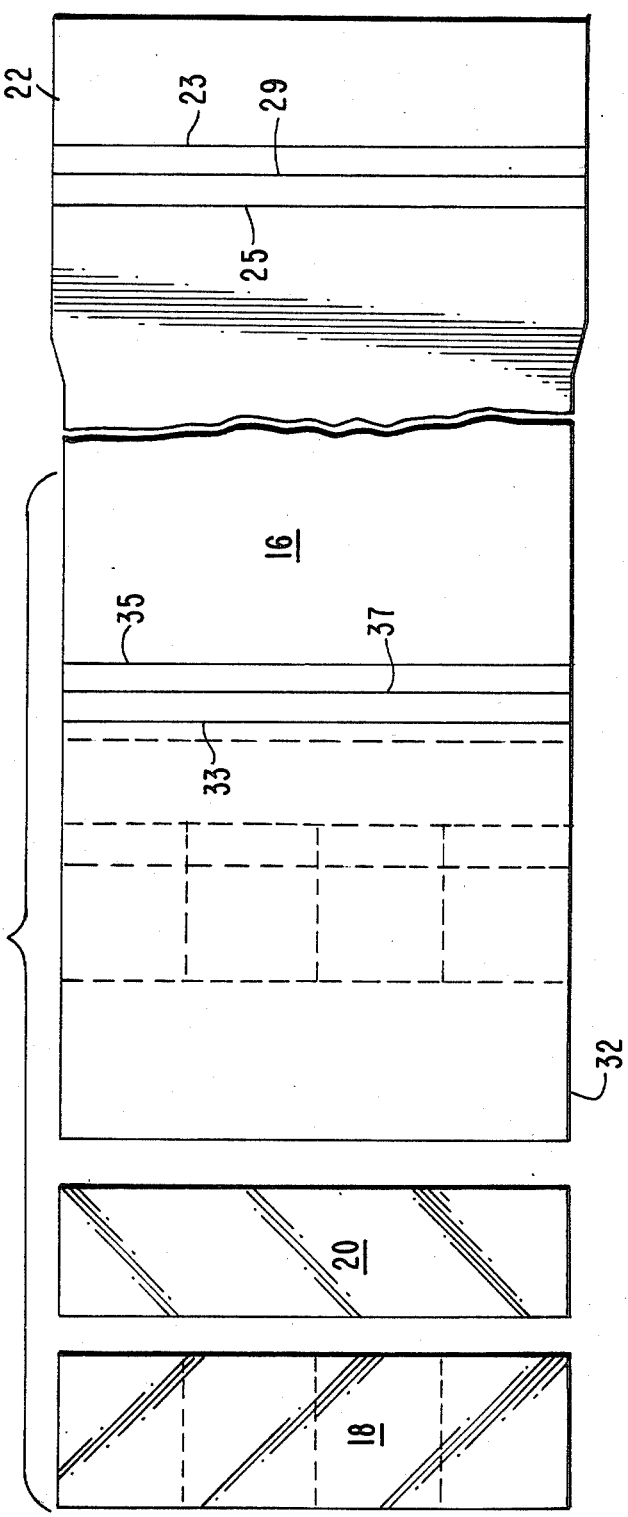
FIG. 3.
FIG. 2.

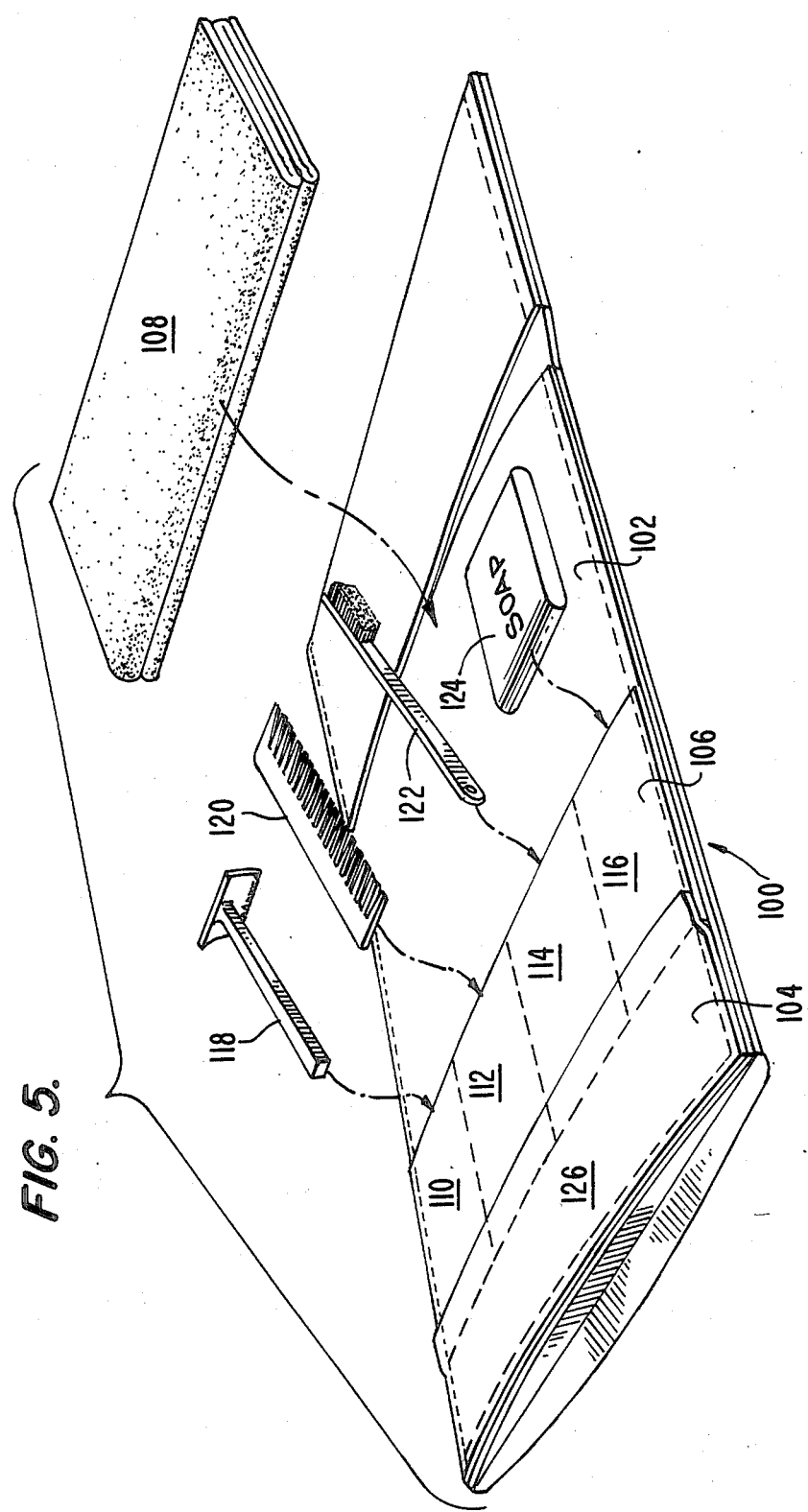

SANITARY, DISPOSABLE BABY CHANGE KIT

BACKGROUND OF THE INVENTION

1. Field of Invention

The present invention pertains generally to kits for retaining sundry products for the care of a baby. More specifically, the present invention relates to an inexpensive, disposable kit that retains toiletries for the care of a baby in a sanitary, tamper-proof fashion.

2. Prior Art

An inexpensive, disposable kit that could be manufactured, and marketed, at a reasonable price has significant commercial potential. Such a kit would find a ready audience among parents, babysitters, nurseries, hospitals, etc. and other segments of the population. A disposable kit, in essence, should appeal to the same persons as presently use disposable diapers, disposable bibs, and other disposable items of this ilk. Furthermore, if the kit were produced in such a manner that the products included therein were maintained in a sanitary condition until usage, the chances of transmitting disease would be considerably reduced, a major consideration for schools, hospitals, day care centers, and the like. Lastly, if the kit were sealed in a tamper-indicating manner, the user would be guaranteed, for all practical purposes, that the contents of the kit had not been adulterated, tainted, or otherwise rendered unsuitable for their intended purposes.

Furthermore, after the seal on the package for the kit has been broken, and the contents of the kit used in the intended fashion, the same package could be re-used to receive, and retain the used disposable diaper and other used baby care products. The configuration of the package could permit the package to be closed, once again, thus avoiding further pollution to the surroundings the person handling the baby, the baby itself, etc. Also the disposition of the soiled material is simplified under improved hygienic conditions.

Whereas the foregoing objectives have been recognized previously, the prior art has not disclosed an inexpensive, disposable, and sanitary kit that achieves such objectives.

For example, U.S. Pat. No. 2,533,850, granted Dec. 12, 1950, to F. P. Syracuse, discloses a handbag having a plurality of compartments, each of which is accessib;e from the exterior of the bag, independently of the other compartments. Each compartment is sealed by a zipper closure. The interior of the bag is lined with a moisture-proof lining, and a partition wall divides the interior into two compartments. One compartment holds clean diapers or clothing, while the other compartment retains soiled diapers.

U.S. Pat. No. 1,606,115, granted Nov. 9, 1926, to G. D. Williams, discloses a baby comfort bag formed of flexible material. A sheet of waterproof material is sewn into the bag to divide the interior of the bag into two compartments. The bag is carried by two spaced handles.

U.S. Pat. No. 4,221,221, granted Sept. 9, 1980, to Jimmie L. Ehrlich, discloses a utility diaper having a plurality of container assemblies connected directly to the diaper. The container assemblies are a plurality of sealed members, each of which is releasably connected to the body of the diaper.

However, none of the foregoing packages has been capable of providing an inexpensive, disposable, single-use kit for retaining the numerous products necessary to change, and cleanse, a baby's bottom, and/or to provide a readily available hygienically safe package for disposing of the soiled diaper and baby care products used in the cleaning operation.

OBJECTS OF THE INVENTION

The prime objective of the present invention is to provide an inexpensive, disposable kit that retains therewithin adequate supplies of powder, moistened towels, oils, and other desirable items, in addition to a and a disposable diaper, so that a baby's bottom may be cleaned and the soiled diaper may be returned to a pouch defined within the kit for ready disposal.

It is another objective of the present invention to design a baby change kit that is compact in its sealed condition, and yet, when opened, contains adequate supplies of the diverse products needed to clean a baby's bottom.

It is yet another objective of the present invention to furnish a tamper-proof seal for the kit, so that any unauthorized tampering with the contents of the kit can be readily detected. Such kit is sanitary and maintains its sanitary state until the seal is destroyed.

Yet another objective is to realize a kit that can easily be adapted to receive men's or women's toiletries, travel accessories, first aid supplies, or the like.

Still another objective is to provide a kit that is folded over itself in such a fashion that the contents of the kit are enveloped within its interior and protected against degradation by contaminants in the atmosphere.

Yet a further objective is to use the plastic package for disposal purposes. The package includes a pouch that receives and retains the soiled diaper and used baby care products after the baby's bottom has been cleaned. The package can be folded over upon itself, thus isolating these materials from any further contact with the baby, the handler for the baby, other babies, and the surrounding environment.

Numerous other objectives that are realized by the instant kit will occur to the skilled artisan when the appended drawings are construed in harmony with the ensuing description of the invention.

BRIEF DESCRIPTION OF THE DRAWINGS

FIG. 1 is a perspective view of a disposable, baby change kit constructed in accordance with the principles of the invention, the kit being shown in its sealed condition;

FIG. 2 is a top plan view of the components of the kit prior to assembling same;

FIG. 3 is a vertical cross-sectional view of the kit, such view being taken along line 3—3 in FIG. 2 and in the direction indicated;

FIG. 4 is an exploded perspective view of the kit, in its opened condition; and

FIG. 5 is a perspective view of a men's toiletries kit constructed in accordance with the principles of the invention.

DESCRIPTION OF PREFERRED EMBODIMENT OF THE INVENTION

Turning now to the drawings, FIGS. 1-4 depict a preferred embodiment of the invention. A kit constructed in accordance with the principles of this invention is identified generally by reference numeral 10, and assumes the form of a baby change kit.

A pressure-sensitive label 12 extends partially across the front of the kit 10 and retains the kit in its sealed, and sanitary, condition. The label recites the various products contained within the kit; for example, in the case of a baby change kit, the label notes that the kit includes a diaper, a packet of baby powder, a packet of petroleum jelly, a pre-moistened towel, a dry towel, soap, and the like.

A tear strip 14 may be incorporated into the label, and the user gains access to the contents of the kit by pulling upwardly on the tear strip, thus severing the label and permitting the kit to be opened. Once the tear strip has been utilized, the label clearly indicates that someone has attempted to gain access to the contents of the kit, and that the sanitary condition of the kit may have been compromised.

While FIG. 1 shows a kit in its folded, and sealed condition, FIG. 2 illustrates the kit 10 prior to forming same. The kit 10 comprises three components of thin plastic film; the components are identified as body 16, first panel 18, and second panel 20. The blank from which body 16 is formed is generally rectangular in shape, but has a leading section 22 that is slightly greater in width than the remainder of the body. The top and bottom surfaces of the body are both finished and decorated.

To form the kit 10 from components 16, 18 and 20, the leading section 22 of body 16 is folded about line 23, and then about line 25. The leading section 22 is then heat-sealed to body 16 along longitudinal lines 24 and 26 (visible in FIG. 4). A bellows fold 28 is formed at one end of the body by flexing inwardly, along line 29, and the fold contributes to the depth of the pocket 30 defined between the folded over portions of leading section 22 and the upper surface of the body 16, as shown in FIG. 3.

The trailing section 32 of the blank that is formed into body 16 is also folded about itself along fold lines 33 and 35 until the edge of section 32 is located a short distance from pocket 30. The trailing section 32 is then heat-sealed to the underlying portion of blank 16 along lines 34, 36. A bellows fold 38 is formed at the end of the body remote from fold 28 by flexing inwardly along line 37, and the fold contributes to the depth of pouch 40 defined between folded over portions of trailing section 32, as shown in FIG. 3.

The first panel 18 may be formed of a rectangle of clear vinyl plastic, while the body 16 is formed of a finished, and visually pleasing, decorated polyethylene film. The panel 18 is approximately equal in width to body 16. The first panel 18 is heat-sealed to body blank 16 along transverse line 42, and is also heat-sealed to body 16 along lines 44 and 46. The panel 18 is subdivided into a plurality of small compartments 48, 50, 52 and 54 by securing the first panel to the underlying body 16 along spaced lines 56, 58 and 60. If desired, the body 16 may be scored or otherwise marked so that the spaced lines at which heat sealing or welding takes place are properly oriented.

The second panel 20, which also is formed of a rectangle of clear vinyl plastic and is equal in width to body blank 16, is then secured to the body 16 along lines 62, 64 and 66. The flap 20 overlaps, to a limited extent, flap 18. A large compartment 68 is formed between the flap 20 and the upper surface of body blank 16, as shown in FIG. 3.

FIG. 4 depicts the manner in which the kit is filled with products for the care of a baby. A coupon 70 is slipped into compartment 68, while compartments 48, 50, 52 and 54 are filled with a dry towel packet 72, a packet of baby powder 74, a wet towel packet 76, and a packet of soap 78. A disposable, paper diaper 80 is inserted into the large pouch 40 defined by the folded over trailing section 32 of the body 16.

After the various body care products are inserted into the various compartments, and into the pouch 40, the trailing section 32 is folded over and slipped into the pocket 30 in the slightly wider leading section 22. The added width of the head facilitates the insertion step. The pressure-sensitive label 12 is then applied. Since the foot section fits neatly within the pocket 30, the kit, in effect, has been folded over itself and the contents of the kit are securely retained within the interior of the kit in a sanitary fashion. Furthermore, because of the relatively simple configuration of the kit, the kit can be used once, and then discarded. The pouch 40 is sized to receive a disposable diaper 80, which, after use, can be re-inserted thereinto. The kit can then be re-sealed and subsequently disposed of in a relatively pollution free manner with a minimum amount of handling.

FIG. 5 suggests an alternative embodiment for the baby change kit shown in FIGS. 1-4. More specifically, the alternative kit 100 comprises a body 102, a first panel 104, and a second panel 106 joined together in the same fashion as kit 10. However, a disposable towel 108, of linen or paper, is inserted into the pouch. The pockets 110, 112, 114 and 116 defined in the first flap 104 by appropriate weld lines, are filled with a disposable razor 118, a comb 120, a toothbrush 12, and a bar of soap 124. Coupons or similar items (not shown) may be inserted into the larger pocket 126. After the body has been filled with the toiletries needed for the kit, the trailing section 128 of the body is folded over and inserted into the slightly larger head 130; a label (not shown) is then applied to the kit to seal same.

The kit may be filled with different items and used for numerous other purposes. For example, the kit could be filled with sample items for a trade show, or might contain medical supplies to serve as an emergency first-aid kit.

Also, while the body of the kit is preferably formed from a 0.003 inch thick sheet of polyethylene, properly slit, folded, and heat-sealed, the same principles may be applied to kits formed of other plastics, executed in cloth, etc.

Diverse other applications will occur to those skilled in the packaging art without departing from the inventive thrust of this application. Consequently, the following claims should not be limited to their literal terms, but should be construed liberally in harmony with the scope and significance of this unique kit.

We claim:
1. A sanitary, disposable baby change kit comprising:
(a) a body comprising a sheet of plastic film with an upper surface and a lower surface,
(b) a leading section and a trailing section situated at opposite ends of said body,
(c) said leading section being folded about itself and being secured to the upper surface of said body to form a pocket,
(d) a first fold being formed across said leading section to define the height of said pocket,
(e) said trailing section being folded about itself and being secured to the upper surface of said body to form a pouch,

(f) a second fold being formed across said trailing section to define the height of said pocket,
(g) said pouch being larger than said pocket,
(h) a diaper received within said pouch,
(i) the lower edge of said pocket being spaced a short distance from the upper edge of said pouch to permit access to said pouch and said diaper received therein when said body is unfolded,
(j) at least one plastic panel secured to said trailing section to define at least one compartment on the upper surface of said trailing section,
(k) baby care products stored within said compartment,
(l) said trailing section being inserted into said pocket after the trailing section has been folded about itself,
(m) sealing means securing the bottom surface of said trailing section to the upper surface of said leading section so that said diaper and said baby care products are enveloped and sealed in a sanitary manner within the confines of the kit prior to using the kit, whereby
(n) a soiled diaper and used baby care products can be re-inserted into said pouch prior to re-folding the kit and disposing of same after using the contents of the kit to clean a baby's bottom.

2. A sanitary disposable baby change kit as defined in claim 1 wherein said sealing means includes a pressure sensitive label and a tear strip extending across said label, the removal of the tear strip serving as a visual indicator that one has attempted to gain access to the contents of the kit.

3. A sanitary, disposable baby change kit as defined in claim 1 wherein said first and said second folds are equal in height so that said pocket and said pouch are substantially equal in height.

* * * * *